US005271406A

United States Patent [19]

Ganguly et al.

[11] Patent Number: 5,271,406

[45] Date of Patent: Dec. 21, 1993

[54] LOW-PROFILE ULTRASONIC TRANSDUCER INCORPORATING STATIC BEAM STEERING

[75] Inventors: Dipankar Ganguly, Redmond; George W. Keilman, Woodinville, both of Wash.

[73] Assignee: Diagnostic Devices Group, Limited, Kirkland, Wash.

[21] Appl. No.: 887,531

[22] Filed: May 22, 1992

[51] Int. Cl.[5] .......... A61B 8/00

[52] U.S. Cl. .......... 128/663.01; 128/662.06; 73/642

[58] Field of Search .......... 128/660.03, 662.06, 128/663.01, 73, 642, 644

[56] References Cited

U.S. PATENT DOCUMENTS

| | | | |
|---|---|---|---|
| 3,387,604 | 2/1966 | Erikson | 310/335 |
| 4,237,729 | 12/1980 | McLeod et al. | 128/662.06 X |
| 4,503,861 | 3/1985 | Entrekin | 128/662.04 |
| 5,167,234 | 12/1992 | Watanabe et al. | 128/660.1 |

*Primary Examiner*—Francis Jaworski
*Attorney, Agent, or Firm*—Christensen, O'Connor, Johnson & Kindness

[57] ABSTRACT

A cylindrical ultrasonic transducer (36) is disclosed. The transducer includes a cylindrical main element (38) provided with a plurality of ring-shaped secondary elements (40 and 42) that are triangular in cross section. By controlling the number, geometry, and construction of the secondary elements, substantially any desired ultrasonic emission pattern can be produced while maintaining a low overall transducer profile.

27 Claims, 4 Drawing Sheets

LOW-PROFILE ULTRASONIC TRANSDUCER INCORPORATING STATIC BEAM STEERING

FIELD OF THE INVENTION

This invention relates generally to ultrasonic transducers and, more particularly, to the profile and acoustic beam patterns of such transducers.

BACKGROUND OF THE INVENTION

Ultrasonic transducers are used in many applications to produce and sense mechanical vibrations in the ultrasonic frequency range. In a number of these applications, it is desirable to use a transducer that has a specific beam pattern. For example, if the transducer is used to monitor the flow of fluid, the beam pattern should define an angle of less than 90 degrees with respect to the direction of fluid flow to ensure a suitable transducer output.

In many instances, it is also desirable for the transducer to be relatively small or have a low profile. For example, a low profile may be necessary to allow the transducer to be introduced into a confined vessel or environment and to reduce the disruptive effect of the transducer on fluid flowing in the vessel.

One particular application of interest for such transducers is the determination of volumetric flow in an intravascular conduit. In that regard, catheter-based ultrasound systems have been developed to determine a patient's cardiac output, i.e., the volumetric flow rate of blood in the patient's pulmonary artery. Such systems employ a transducer positioned close to the distal end of a catheter. This transducer is connected to a termination assembly at the proximal end of the catheter by electrical wires threaded through one or more of the catheter lumens. A bedside monitor attached to the termination assembly applies a high-frequency electrical signal (typically in the megahertz range) to the transducer, causing it to emit ultrasonic energy. Some of the emitted ultrasonic energy is then reflected by the blood cells flowing past the catheter and returned to the transducer. This reflected and returned energy is shifted in frequency in accordance with the Doppler phenomenon.

The transducer converts the Doppler-shifted, returned ultrasonic energy to an output electrical signal. This output electrical signal is then received by the bedside monitor via the lumen wiring and is used to quantitatively detect the amplitude and frequency-shifted Doppler signal associated with the ultrasonic energ reflected from the moving blood cells.

The shifted frequency of the reflected and returned energy is proportional to the cosine of the angle between the ultrasonic beam and the direction of blood flow. Thus, if the angle between the ultrasonic beam and direction of blood flow is 90 degrees, there will be no shift in frequency and, hence, no Doppler output signal. As a result, the ultrasonic beam must be launched at an angle of less than 90 degrees with respect to the blood flow.

Existing ultrasonic measurement systems process the amplitude and frequency shift information electronically to estimate the average velocity of the blood flowing through the conduit in which the transducer-carrying catheter is inserted. Such systems also require that an independent estimation of the cross-sectional area of the conduit be made using one of a variety of techniques taught in the literature, including, for example, the approach disclosed in U.S. Pat. No. 4,802,490. Cardiac output is then computed by multiplying the average velocity and cross-sectional area estimates.

As will be appreciated, the ultrasonic transducer used in such an intra-vascular application must be sufficiently small to positioned in the intravascular conduit. In addition, the transducer should emit ultrasonic energy at an angle of less than 90 degrees with respect to the direction of blood flow. Further, the surface of the transducer from which ultrasonic energy is emitted and received should not disrupt the blood flow, to avoid affecting the cardiac output determination. In view of these observations, it would be desirable to provide an ultrasonic tranducer having a low profile, for use in limited spaces and to achieve minimal flow disruption.

SUMMARY OF THE INVENTION

In accordance with this invention, a transducer for emitting energy in response to an input signal is disclosed. The transducer includes a main element having an input region for receiving an input signal and a launch surface from which the energy is emitted. A plurality of secondary elements are positioned on the launch surface of the main element for controlling the manner in which the energy is emitted. The secondary elements may, for example, include a pair of elements that cooperatively define a path for energy emitted from the launch surface of the substrate. Alternatively, the secondary elements may include a first set of elements distributed across the launch surface of the substrate.

In a preferred arrangement, the transducer has a low profile and is designed to emit ultrasonic waves in a predetermined pattern in response to an input electric signal. The transducer includes a roughly cylindrical substrate having an input region for receiving the input electric signal and a launch surface from which the ultrasonic waves are emitted at a first angle. A first plurality of aligned, ring-shaped secondary elements, roughly triangular in cross section, are positioned on the launch surface of the substrate to cause the ultrasonic waves to be emitted at a second angle. A second plurality of aligned, ring-shaped secondary elements, roughly triangular in cross section, are positioned on the first plurality of secondary elements to cause the ultrasonic waves to be emitted at a launch angle.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
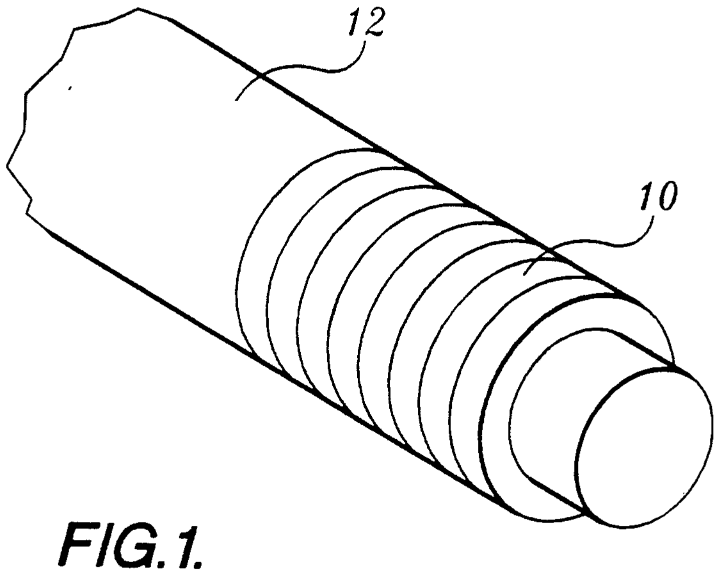
FIG. 1 is an illustration of a cylindrical embodiment of a transducer constructed in accordance with the invention.

Referring now to FIG. 1, a first embodiment 10 of an ultrasonic transducer constructed in accordance with this invention is shown. The transducer 10 is attached to the end of a catheter 12 for use, for example, in determining cardiac output. This transducer embodiment, as well as others described below, preferably includes elements that statically steer the transducer beam pattern, allowing a desired beam pattern to be achieved with a relatively low transducer profile.

Figure 2:
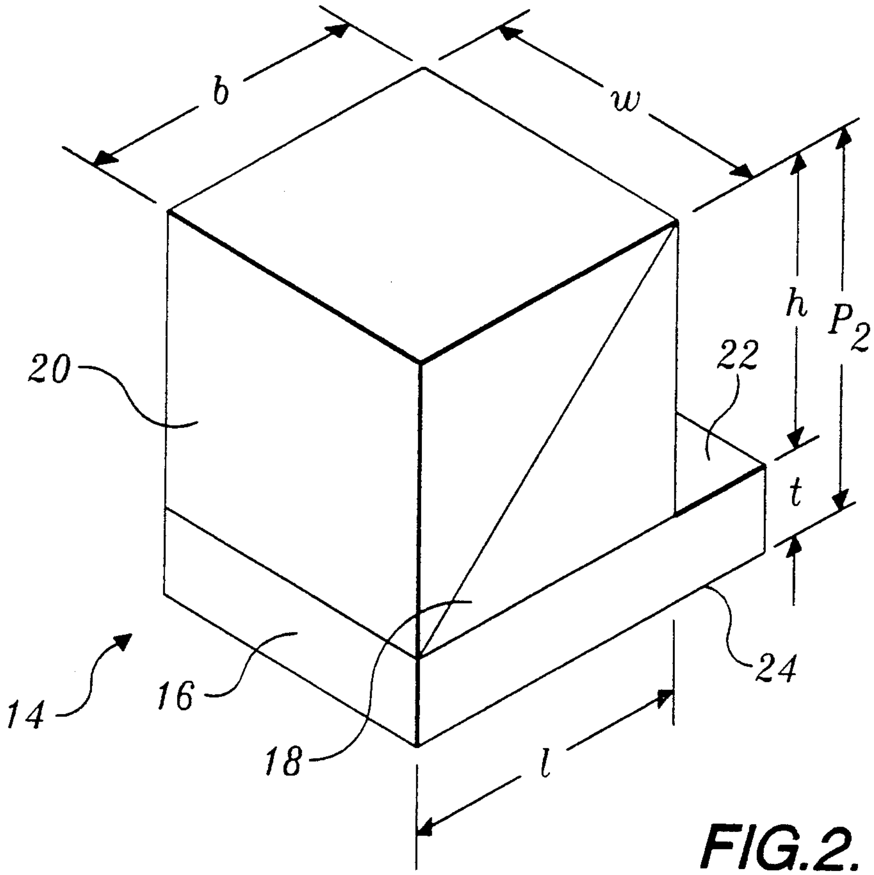
FIG. 2 is an illustration of a simpler embodiment of a transducer constructed in accordance with this invention.
Figure 3:
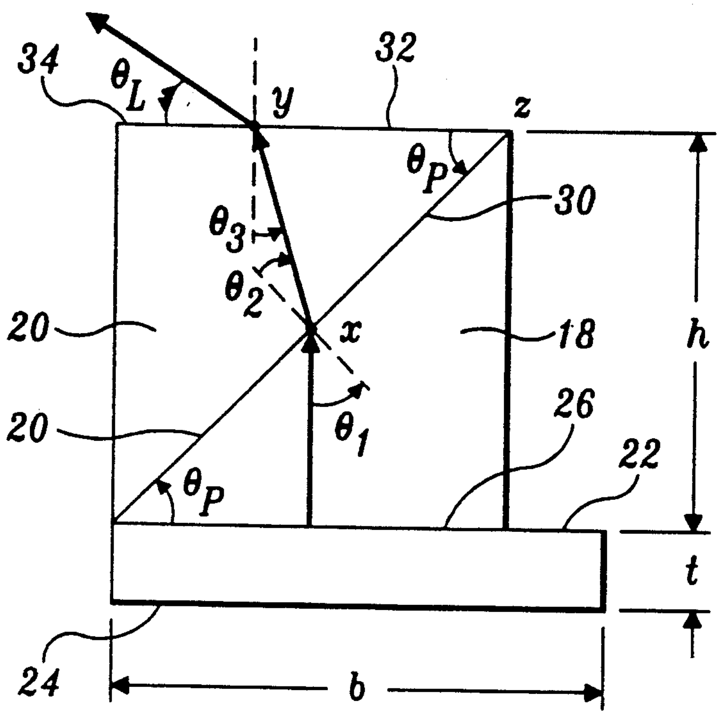
FIG. 3 is a side view of the transducer of FIG. 2.

Before discussing the construction of transducer 10 in detail, the principle behind transducer 10 will be reviewed. In that regard, FIGS. 2 and 3 illustrate a more elemental embodiment 14 of the transducer. As shown, this transducer 14 includes a substrate 16, a first prism 18, and a second prism 20. Cooperatively, the first and second prisms 18 and 20 allow the desired beam pattern to be achieved, while maintaining a low transducer profile.

The substrate 16 is a block of piezoelectrical material having an "active" length l and thickness t. Substrate 16 includes a top face 22 and bottom face 24. At an "inactive" end, the top and bottom faces 22 and 24 are connected to wires leading to a source of electrical energy (not shown in FIG. 2) by, for example, a conductive adhesive.

The first prism 18 is made of an acoustically conductive material and has an input face 26 and an output face 28. The input face 26 of prism 18 is coupled to the top face 22 of substrate 16 and the input face 26 and output face 28 form an angle $\theta_p$ with respect to each other. The first prism 18 has a length b and a height h.

The material selected for the first prism 18 is designed to ensure that most of the acoustic energy applied to the input face 26 of prism 18 is transmitted through prism 18 to the output face 28 in the form of a refracted wavefront. The material of prism 18 should also be selected to ensure that the velocity of propagation of a refracted acoustic wavefront in the prism 18 is greater than the velocity of propagation of a wavefront in prism 20, and that an acoustic wave propagating in prism 18 is not attenuated (damped out) significantly. A suitable material is, for example, Castall 341 FR/RT1 manufactured by General Electric Co.

The second prism 20 is also made of an acoustically conductive material and has an input face 30 and an output face 32. The input face 30 of prism 20 is coupled to the output face 28 of prism 18 and prism 20 is geometrically identical to prism 18. In that regard, the input face 30 and output face 32 of prism 20 form an angle $\theta_p$ with respect to each other. Like prism 18, the second prism 20 also has a length b and height h.

The prism 20 is made of a material selected to ensure that most of the acoustic energy applied to the input face 30 of prism 20 is transmitted through prism 20 to the output face 32 in the form of a refracted wavefront. The material of prism 20 should also be selected to ensure that the velocity of propagation of refracted acoustic wavefront in prism 20 is less than the velocity of propagation of a wavefront in prism 18 and greater than or equal to the velocity of propagation of a wavefront through the medium (for example, blood, during clinical use) adjacent prism 20. Finally, the material of prism 20 should be selected to ensure that an acoustic wave propagating in prism 20 is not attenuated significantly. A suitable material is, for example, RTV Silicone.

Discussing now the interaction of components 16, 18, and 20, as noted previously, a source of electrical energy is coupled to the top and bottom faces 22 and 24 of substrate 16. With an electrical signal having an ultrasonic frequency applied between faces 22 and 24, the piezoelectric substrate 16 expands and contracts in thickness t, causing a compressional pressure wave to propagate in the prism 18 adjacent substrate 16. This compressional pressure wave propagates perpendicular to the top face of substrate 16 and the input face 26 of prism 18.

The compressional wave impinges upon the output face 28 of prism 18 at an angle of $\theta_1$ measured from a line perpendicular to output face 28. At the interface between the output face 28 of prism 18 and the input face 30 of prism 20, the compressional pressure wave undergoes a refraction. The direction of propagation of the wave as it enters the prism 20 changes to an angle $\theta_2$ measured from a line perpendicular to the input face 30 of prism 20, as will be described in greater detail below.

The refracted compressional wave then travels through prism 20 without additional refraction until it encounters the interface between the output face 32 of prism 20 and the adjacent fluid. At this interface, the compressional wave undergoes a second refraction and the direction of propagation again changes to an angle $\theta_L$ defined with respect to a launch face 34 of transducer 14. This angle may be referred to as the transducer beam angle or launch angle.

After leaving the transducer 14, the compressional wave encounters scatters suspended in the flowing fluid and is back-scattered or returned to the output face 32 of prism 20. Due to the reciprocal nature of the wave's propagation through transducer 14, the compressional wave will reach the top face 22 of substrate 16 by following a path that is the exact duplicate, in reverse, of the path followed by the outgoing waves. Once back at the substrate 16, the compressional waves vibrate substrate 16 in its thickness mode and substrate 16 thus converts the waves back into electrical signals.

Discussing now the manner in which a particular beam angle $\theta_L$ can be achieved, assume that the speed of sound in the first prism 18 is $v_1$, the speed of sound in the second prism 20 is $v_2$, and the speed of sound in the blood, or other fluid whose velocity is to be measured, is $v_b$. Addressing the interrelationship of the various parameters affecting the operation of transducer 14, we first know that:

$$\theta_1 = \theta_p \quad (1)$$

As will be appreciated from FIG. 2 and Snell's Law:

$$\frac{\sin\theta_1}{\sin\theta_2} = \frac{v_1}{v_2} = n \quad (2)$$

and by solving Equation (2) for $\theta_2$:

$$\theta_2 = \sin^{-1}\left(\frac{v_2}{v_1}\sin\theta_1\right) \quad (3)$$

Next, summing the included angles of triangle xyz in FIG. 3, we have:

$$\theta_1+(90-\theta_2)+(90-\theta_3)=180 \quad (4)$$

and, solving for $\theta_3$, yield:

$$\theta_3=\theta_1-\theta_2 \quad (5)$$

Then, returning to Snell's Law, we have:

$$\frac{\sin(90-\theta_L)}{\sin\theta_3}=\frac{v_b}{v_2} \quad (6)$$

and, by solving Equation (6) for $\theta_L$:

$$\theta_L=\cos^{-1}\left(\frac{v_b}{v_2}\sin\theta_3\right) \quad (7)$$

Substituting Equations (1), (3), and (5) into Equation (7) yields:

$$\theta_L=\cos^{-1}\left(\frac{v_b}{v_2}\sin\left(\theta_p-\sin^{-1}\left(\frac{v_2}{v_1}\sin\theta_1\right)\right)\right) \quad (8)$$

Next, as will be appreciated from FIG. 3, simple trigonometry establishes that:

$$\theta_p=\tan^{-1}(h/b) \quad (9)$$

and substituting Equation (9) into Equation (8) yields:

$$\theta_L= \cos^{-1}\left(\frac{v_b}{v_2}\sin\left(\tan^{-1}(h/b)-\sin^{-1}\left(\frac{v_2}{v_1}\sin(\tan^{-1}(h/b))\right)\right)\right) \quad (10)$$

As will be appreciated, the variables in Equation (10) are a function of the construction and composition of prisms 18 and 20. Thus, by carefully designing prisms 18 and 20, the desired effective launch angle $\theta_L$ can be obtained for the transducer 14.

As will be appreciated from FIG. 3, with two prisms 18 and 20 employed, the launch angle $\theta_L$ is the result of two refractions of the ultrasonic wave. If only one prism 18 (having the same geometry as prism 18 in FIG. 3) were employed, however, the wave would undergo a single refraction and the magnitude of the launch angle would be greater. More particularly, the effective launch angle $\theta'_L$ defined with respect to the top face 22 of substrate 16 would be:

$$\theta'_L=(90-\tan^{-1}(h/b))+\sin^{-1}\left(\frac{v_b}{v_1}+\sin(\tan^{-1}(h/b))\right) \quad (11)$$

Thus, by adding the second prism 20 in the manner shown in FIGS. 2 and 3, the beam angle can be reduced. While this could also be accomplished by using a single prism 18 with a greater ratio of h/b, the two-prism arrangement of FIGS. 2 and 3 allows the reduced beam angle to be achieved without increasing prism and, hence, transducer height, maintaining a low overall transducer profile.

Figure 4:
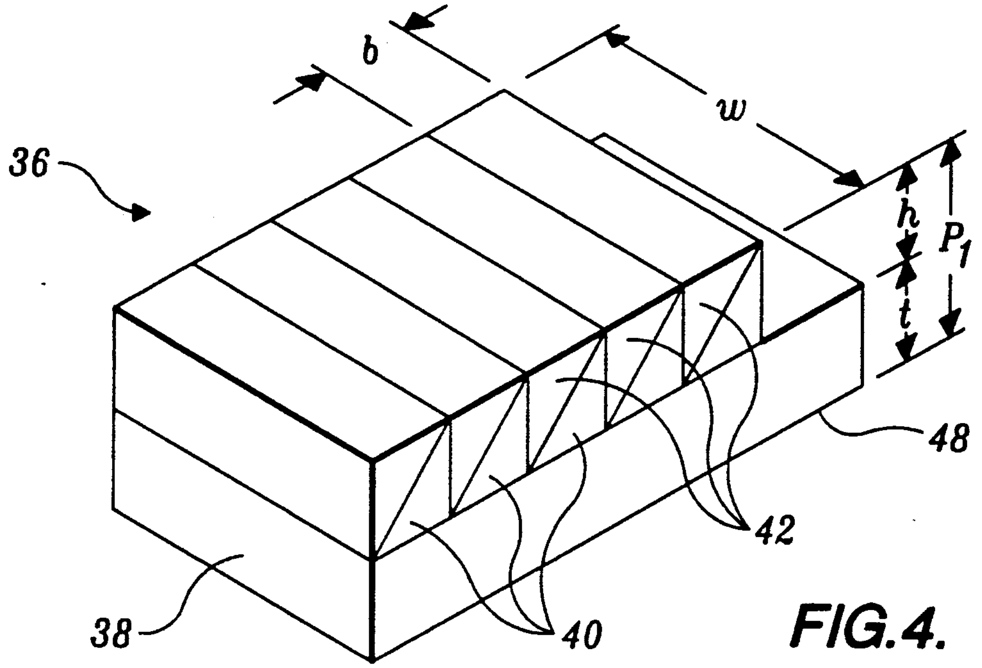
FIG. 4 is an illustration of an embodiment of a transducer constructed in accordance with this invention that is more complex than the embodiment of FIG. 2.
Figure 5:
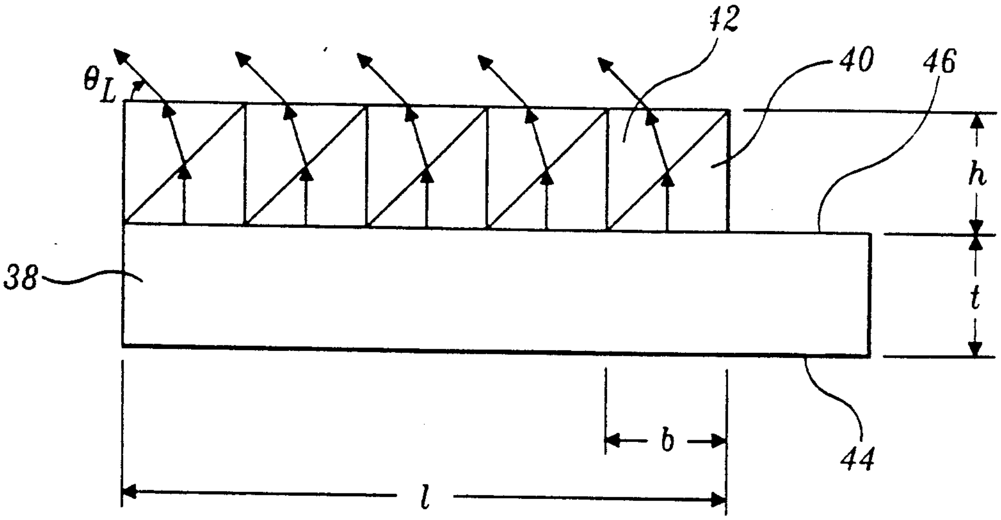
FIG. 5 is a side view of the transducer of FIG. 4.

Having reviewed the elemental embodiment 14 of the transducer shown in FIG. 2, a more complicated embodiment 36 of the transducer will now be considered. As shown in FIGS. 4 and 5, transducer 36 includes a main element or substrate 38 and a plurality of first prisms 40 and second prisms 42. The substrate 38 is preferably a piezoelectric block of, for example, lead zirconate titanate (PZT) having an "active" length l, thickness t, and width w.

Substrate 38 includes a bottom face 44 and a top face 46, and at one end includes an "inactive" region 48 at which electrical signals are applied to and received from the transducer 36.

The prisms 40 and 42 are formed of acoustically conductive materials, of the same type described in connection with FIG. 2 above. In that regard, each one of the first prisms 40 corresponds to the first prism 18 of FIG. 2, while each one of the second prisms 42 corresponds to second prism 20. In the arrangement shown in FIG. 4, all of the prisms 40 are of identical construction and have a width w, height h, and length b. Similarly, all of the prisms 42 are of identical construction, having width w, height h, and length b. As shown, the first prisms 40 are aligned or oriented in the same manner without interruption along substantially the entire active length l of substrate 38. The second prisms 42 are also aligned in the same manner, but inverted and reversed with respect to the first prisms 18 to fill the spaces between prisms 40.

As will be appreciated from the earlier discussion of FIGS. 2 and 3, the first and second prisms 40 and 42 of transducer 36 effectively "bend" the ultrasonic waves emitted and received by transducer 16 twice to produce the desired beam angle $\theta_L$. More particularly, instead of having a beam angle that is perpendicular to the top face 46 of substrate 38, as would occur if substrate 38 were used alone, the prisms 40 and 42 cooperatively bend the waves to an effective beam angle $\theta_L$. By appropriately selecting the number, geometry, and construction of prisms 40 and 42, the desired beam angle can be obtained.

In addition to allowing a desired beam angle $\theta_L$ to be obtained, this arrangement allows the profile $P_1$ of transducer 36 to be controlled. In that regard, if only set of prisms is employed, as shown in FIG. 2, the length b of the prisms would necessarily be equal to the active length l of the substrate. In the arrangement shown in FIG. 4, however, a plurality m of prisms 40 and prisms 42 are distributed across the active length l of substrate 38. Thus, the length b of each prism 40 and 42 is equal to l/m.

As will be appreciated from Equations (10) and (11), the launch angle or beam angle $\theta_L$ is a function of the ratio h/b. Thus, if the same launch angle $\theta_L$ is to be produced by the transducers shown in FIGS. 2 and 4, the h/b ratio of the prisms used in the two embodiments must be the same. Because the length b of the prisms 18 and 20 in FIG. 2 is greater than the length b of the prisms 40 and 42 in FIG. 4, the height h of the prisms 18 and 20 would also need to be proportionally larger (i.e., by a factor of m) than that of prisms 40 and 42.

Thus, the single-pair transducer 14 of FIG. 2 would have a profile $P_2$ equal to t+(nh), whereas the transducer 36 of FIG. 4 would have a profile $P_1$ equal to t+h. This multiple-pair arrangement has been found suitable for a wide number m of prisms 40 and 42 and a broad range of launch angles $\theta_L$, with only limited interference between the ultrasonic emission and reception by adjacent prisms 40 and adjacent prisms 42 experienced.

In summary, the profile of the transducer can be advantageously reduced both by employing paired prisms and by distributing a number of prisms across the substrate. The most pronounced reduction in transducer profile is achieved, however, by combining the two techniques to provide a plurality of paired prisms across the transducer.

Figure 6:
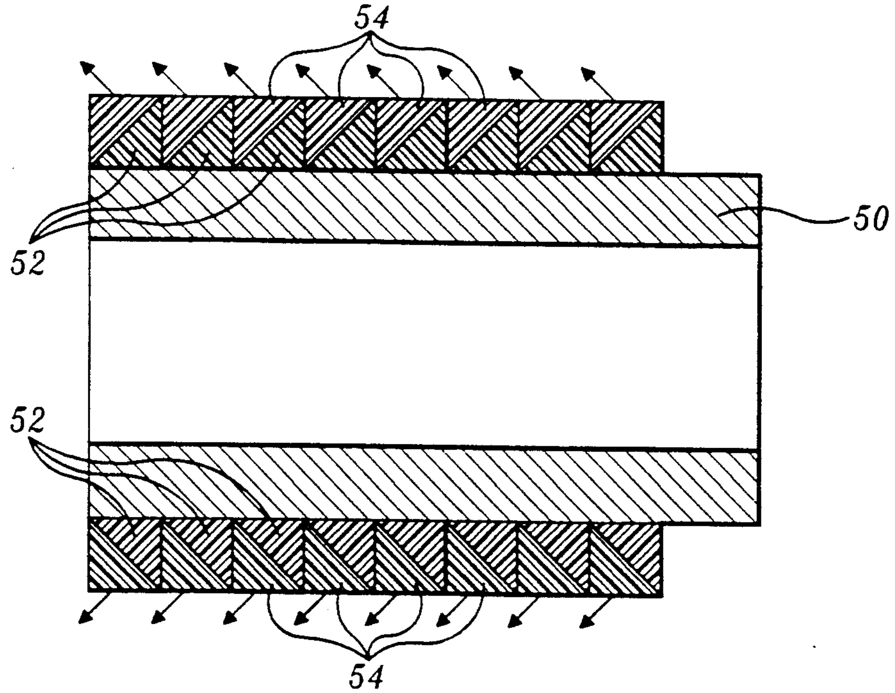
FIG. 6 is a side view of an alternative construction of the transducer of FIG. 4.

Although the preceding discussion was in the context of identically constructed prisms 40 and prisms 42 producing a uniform emission pattern, as will be appreciated, a transducer having a nonuniform emission pattern can also be constructed in accordance with this invention. For example, the geometry of prisms 40 and 42 could be varied across the substrate 38 as shown in FIG. 6. In that regard, as will be appreciated, the prisms 40 and 42 having the highest h/b ratio (which is inversely proportional to the effective launch angle $\theta_L$) would be placed nearest the left side of the substrate 38 in the configuration shown in FIG. 6, with those prisms 40 and 42 having progressively lower h/b ratios extending to the right. As a result, the effective beam angle of the transducer would become progressively larger from left to right, minimizing the interference from adjacent prisms 40 and 42. Alternatively, the geometry of the prisms 40 and 42 could be identical, with different materials employed to create a nonuniform emission pattern across the transducer.

As will be recalled from the earlier discussion of the transducer 14 shown in FIG. 2, although paired prisms 18 and 20 allow a given beam angle $\theta_L$ to be achieved with a low overall transducer height, a single-prism transducer 14 could be employed. The same principle applies to the transducer 36 shown in FIG. 4, where the second prisms 42 could be omitted.

Figure 7:
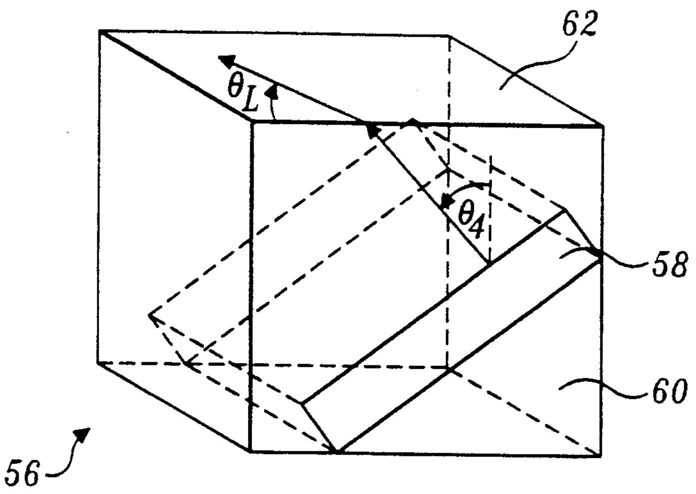
FIG. 7 is an illustration of another alternative embodiment of the transducer of FIG. 2.

Another alternative embodiment of a transducer employing a single prism is shown in FIG. 7. In that regard, the transducer 56 illustrated in FIG. 7 includes a piezoelectric substrate 58 positioned on an inclined backing layer 60 of, for example, epoxy mixed with glass microballoons. A layer of acoustically conductive material 62, corresponding to one of the prisms described above, is then placed over the substrate 58, enclosing the electrical connections made to the substrate (not illustrated in FIG. 7). By inclining the substrate 58 with respect to the top surface of transducer 62, compressional waves are propagated in material 62 at an angle $\theta_4$, with the interface between material 62 and the surrounding fluid additionally refracting the waves to the desired launch angle $\theta_L$.

As will be appreciated, the structure of FIG. 7 can also be repeated to form a transducer including a plurality of inclined piezoelectric substrates 50, if desired. By including a number of small substrates rather than one large one, the same launch angle can be maintained while advantageously offering a lower transducer profile.

Reviewing the relative advantages and disadvantages of the various "single-prism" embodiments of transducers 14, 36, and 56 described above, as will be appreciated from FIG. 3, the omission of prism 20 from transducer 14 would result in a larger effective launch angle $\theta_L$, equal to the sum of $\theta_2$ and 90 degrees. While the launch angle $\theta_L$ could be decreased by increasing $\theta_p$, the profile of transducer 14 would consequently increase. The omission of prisms 42 from the transducer 36 of FIG. 4 would also require the use of a transducer 36 having a higher profile to achieve the same launch angle $\theta_L$, although the use of a plurality of prisms 40 allows a lower profile to be achieved than if a single prism 18 were employed as in FIG. 2. The arrangement of FIG. 7 has the advantages of allowing a relatively low launch angle $\theta_L$ to be achieved and including an exposed surface that is parallel to, and nondisruptive of, the surrounding fluid flow.

Figure 8:
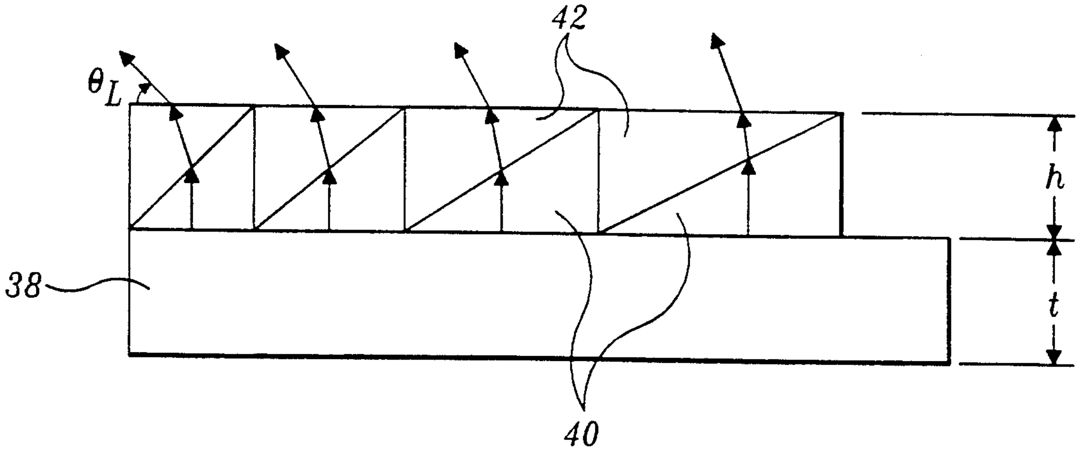
FIG. 8 is a sectional view of the transducer of FIG. 1.

Returning finally to the embodiment 10 of the transducer shown in FIG. 1, this transducer 10 is constructed in roughly the same manner as that shown in FIG. 4 except that, now, the substrate 50 is a cylindrical element and the first and second prisms 52 and 54 are rings having triangular cross sections. This configuration is shown in greater detail in the sectional view of FIG. 8 and produces a conical beam at a launch angle $\theta_L$ defined with respect to the axis of the cylindrical substrate 50.

As shown in FIG. 1, the transducer 10 is coupled to the end of a catheter 12 for intravascular use. The catheter 12 is of the type described in the Johnston patent above and is intended into vascular conduits. The catheter 12 is electrically and mechanically coupled to a processing system (not shown), which controls catheter 12 and transducer 10 and determines cardiac output.

As will be appreciated, this embodiment of the transducer 10 allows the transducer 10 to emit a conical beam of ultrasonic energy, while maintaining a generally cylindrical construction. Thus, in addition to producing the desired launch angle $\theta_L$ and having the desired profile, the transducer 10 has a relatively smooth surface that minimizes disruption of the fluid flow to be monitored.

The actual construction of transducers of the type described above can be accomplished in several different ways. For example, the prisms can be made of epoxy that is cast onto the substrate with appropriate molding tools. Alternatively, the substrate and first prisms could, for example, be etched or machined from a blank.

Those skilled in the art will recognize that the embodiments of the invention disclosed herein are exemplary in nature and that various changes can be made therein without departing from the scope and the spirit of the invention. In this regard, and as was previously mentioned, the invention is readily embodied with either slab or cylindrical transducers. Further, it will be recognized that any number of identical or consecutively different secondary elements can be employed. In addition, the transducers are suitable for nonmedical applications, including industrial process control. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A transducer for emitting energy in response to an input signal, the energy being emitted at a predetermined angle, said transducer comprising:

a substrate having an input region for receiving the input signal and a launch surface from which the energy is emitted; and a plurality of secondary elements arranged in at least one of two configurations, including a first configuration in which the plurality of secondary elements are distributed across said launch surface of said substrate, and a second configuration in which at least two secondary elements are stacked, for causing the energy to be emitted from said transducer at said predetermined angle.

2. The transducer of claim 1, wherein said secondary elements comprise similarly-dimensioned first and second elements, each including an input surface and a launch surface, said input surface of said first element being coupled to said launch surface of said substrate, said input surface of said second element being coupled to said launch surface of said first element, said launch surface of said first element defining an acute angle with respect to said launch surface of said substrate and said launch surface of said second element being substantially parallel to said launch surface of said substrate, said first and second elements cooperatively defining a path for energy emitted from said launch surface of said substrate.

3. The transducer of claim 1, wherein said secondary elements comprise a first set of elements distributed across said launch surface of said substrate, each said secondary element including an input surface and a launch surface, said input surfaces of said secondary elements being coupled to said launch surface of said substrate, and said launch surfaces of said secondary elements being substantially parallel to each other.

4. The transducer of claim 3, wherein said secondary elements further comprise a second set of elements positioned adjacent said first set of elements, each said element of said second set including an input surface and a launch surface, said input surfaces of said elements of said second set being coupled to different ones of said launch surfaces of said elements of said first set.

5. The transducer of claim 1, wherein said secondary elements are roughly triangular in cross section.

6. The transducer of claim 1, wherein said substrate is a generally cylindrical member.

7. The transducer of claim 6, wherein said secondary elements are ring-shaped members that are roughly triangular in cross section.

8. The transducer of claim 1, wherein the energy is emitted as ultrasonic waves and the input signal is an electric signal.

9. The transducer of claim 8, wherein the ultrasonic waves are emitted from said launch surface of said substrate at a first angle.

10. The transducer of claim 9, wherein said plurality of secondary elements causes the ultrasonic waves to be emitted at a second angle.

11. The transducer of claim 10, wherein said plurality of secondary elements causes the ultrasonic waves to undergo two refractions.

12. The transducer of claim 10, wherein said plurality of secondary elements allows said transducer to emit ultrasonic waves at said second angle and allows said transducer to have a profile that is smaller than would occur if a single secondary element were used to emit ultrasonic waves at said second angle.

13. The transducer of claim 1, wherein said secondary element alters the angle at which energy is emitted relative to the launch surface.

14. The transducer of claim 13, wherein said secondary element allows said transducer to emit energy at a predetermined angle and allows said transducer to have a profile that is smaller than would occur if the substrate were altered to emit energy at the predetermined angle.

15. The transducer of claim 1, wherein said transducer has an axis, said launch surface of said substrate being inclined relative to said axis.

16. The transducer of claim 15, further comprising a plurality of said substrates.

17. A low-profile transducer for emitting ultrasonic waves in a predetermined pattern in response to an input electric signal, said transducer comprising:

a roughly cylindrical substrate having an input region for receiving the input electric signal and a launch surface from which the ultrasonic waves are emitted at a first angle;

a first plurality of aligned ring-shaped secondary elements, roughly triangular in cross section, positioned on said launch surface of said cylindrical substrate for causing the ultrasonic waves to be emitted at a second angle; and a second plurality of aligned ring-shaped secondary elements, roughly triangular in cross section, positioned on said first plurality of aligned ring-shaped secondary elements for causing the ultrasonic waves to be emitted at a launch angle in the predetermined pattern.

18. The transducer of claim 17, wherein said first angle is 90 degrees.

19. The transducer of claim 17, wherein said substrate is a piezoelectric material.

20. The transducer of claim 19, wherein said piezoelectric material is lead zirconate titanate.

21. The transducer of claim 17, wherein said first plurality of secondary elements are made of Castall 341 FR/RT1 and said second plurality of secondary elements are made of RTV silicone.

22. The transducer of claim 17, wherein said substrate and said first and second pluralities of secondary elements cooperatively allow said transducer to have a generally cylindrical shape and to emit ultrasonic waves in a generally conical pattern.

23. A method of producing an ultrasonic wave emission pattern, comprising the steps of:

applying an electric signal to a piezoelectric substrate having a launch surface, said substrate emitting ultrasonic waves from said launch surface in response to said electric signal; and employing a plurality of secondary prismatic elements, coupled to the substrate, and arranged in at least one of two configurations, including a first configuration in which a plurality of secondary prismatic elements are distributed across said launch surface and a second configuration in which at least two secondary elements are stacked, to bend the ultrasonic waves to have a desired launch angle and to give the transducer a desired profile.

24. The method of claim 23, wherein a pair of said prismatic elements are employed to bend the ultrasonic waves twice.

25. A transducer for emitting energy in response to an input signal, the energy being emitted at a predetermined angle relative to said transducer, said transducer comprising:

an electrically monolithic substrate for emitting energy in response to an input signal applied thereto and having a launch surface from which the energy is emitted; and a plurality of secondary elements coupled proximate to said launch surface of said substrate for causing, said plurality of secondary elements being configured as adjacent prisms shaped so as to cause the energy to be emitted from said transducer at said predetermined angle.

26. The transducer of claim 25, wherein said secondary elements comprise similarly dimensioned first and second elements, each including an input surface and a launch surface, said input surface of said first element being coupled to said launch surface of said substrate, said input surface of said second element being coupled to said launch surface of said first element.

27. The transducer of claim 25, wherein said secondary elements comprise a first set of elements distributed across said launch surface of said substrate, each said secondary element including an input surface and a launch surface, said input surfaces of said secondary elements being coupled to said launch surface of said substrate, and said launch surfaces of said secondary elements being substantially parallel to each other.

* * * * *

UNITED STATES PATENT AND TRADEMARK OFFICE

CERTIFICATE OF CORRECTION

PATENT NO. : 5,271,406

DATED : December 21, 1993

INVENTOR(S) : D. Ganguly et al.

It is certified that error appears in the above-indentified patent and that said Letters Patent is hereby corrected as shown below:

| COLUMN | LINE | |
|---|---|---|
| [56] | 5th Ref. | Please add --3,325,779 6/1967 D. L. Supernaw et al.-- |
| [56] | 6th Ref. | Please add --4,327,738 5/1982 P. S. Green et al.-- |
| [56] | 7th Ref. | Please add --4,582,067 4/1986 F. E. Silverstein et al.-- |
| [56] | 8th Ref. | Please add --4,605,009 8/1986 L. Pourcelot et al.-- |
| [56] | 9th Ref. | Please add --4,637,401 1/1987 G. G. Johnston-- |
| [56] | 10th Ref. | Please add --4,665,925 5/1987 H. D. Millar-- |
| [56] | 11th Ref. | Please add --4,674,336 6/1987 G. G. Johnston-- |
| [56] | 12th Ref. | Please add --4,697,595 10/1987 G. Breyer et al.-- |
| [56] | 13th Ref. | Please add --4,722,347 2/1988 J. H. Abrams et al.-- |
| [56] | 14th Ref. | Please add --4,732,156 3/1988 T. Nakamura-- |
| [56] | 15th Ref. | Please add --4,733,669 3/1988 J. Segal-- |

UNITED STATES PATENT AND TRADEMARK OFFICE

CERTIFICATE OF CORRECTION

PATENT NO. : 5,271,406
DATED : December 21, 1993
INVENTOR(S) : D. Ganguly et al.

It is certified that error appears in the above-indentified patent and that said Letters Patent is hereby corrected as shown below:

| COLUMN | LINE | |
|---|---|---|
| [56] | 16th Ref. | Please add --4,757,821 7/1988 J. E. Snyder-- |
| [56] | 17th Ref. | Please add --4,890,624 1/1990 D. Ganguly et al.-- |
| [56] | 1st Ref. | Please add --1288961 2/1969 Germany-- |
| 1 | 50 | "energ" should read --energy-- |
| 2 | 5 | after "to" insert --be-- |
| 3 | 61 | after "propagation of" insert --a-- |
| 4 | 34 | "scatters" should read --scatterers-- |
| 6 | 41 | after "only" insert --one-- |
| 8 | 20 | after "intended" insert --for insertion-- |
| 10 (Claim 25 | 64 Line 10) | after "substrate" delete "for causing" |

Signed and Sealed this

Fourteenth Day of June, 1994

Attest:

BRUCE LEHMAN

*Attesting Officer* — *Commissioner of Patents and Trademarks*